(12) United States Patent
Schmied et al.

(10) Patent No.: US 8,151,830 B2
(45) Date of Patent: Apr. 10, 2012

(54) SENSING APPARATUS

(75) Inventors: Ralf Schmied, Freiberg (DE); Werner Runft, Winnenden (DE)

(73) Assignee: Robert Bosch GmbH, Stuttgart (DE)

( * ) Notice: Subject to any disclaimer, the term of this patent is extended or adjusted under 35 U.S.C. 154(b) by 1069 days.

(21) Appl. No.: 12/064,400

(22) PCT Filed: Jul. 24, 2006

(86) PCT No.: PCT/EP2006/064575
§ 371 (c)(1),
(2), (4) Date: Feb. 21, 2008

(87) PCT Pub. No.: WO2007/023055
PCT Pub. Date: Mar. 1, 2007

(65) Prior Publication Data
US 2008/0230145 A1    Sep. 25, 2008

(30) Foreign Application Priority Data
Aug. 23, 2005 (DE) .......................... 10 2005 039 765

(51) Int. Cl.
*B65B 1/30* (2006.01)
(52) U.S. Cl. ................... 141/83; 141/71; 356/338
(58) Field of Classification Search ............ 141/12, 141/71, 73, 81, 83, 94; 356/51, 338; 425/169
See application file for complete search history.

(56) References Cited

U.S. PATENT DOCUMENTS

| | | | | |
|---|---|---|---|---|
| 3,303,537 A * | 2/1967 | Mislan | ........................ | 164/154.4 |
| 5,371,366 A * | 12/1994 | Marui | .............................. | 850/12 |
| 5,591,461 A | 1/1997 | Komatsu et al. | | |
| 6,425,422 B1 * | 7/2002 | Trebbi | ............................ | 141/67 |
| 6,592,355 B2 * | 7/2003 | Kachnic | ......................... | 425/169 |
| 7,099,015 B2 * | 8/2006 | Melnyk | ......................... | 356/480 |
| 7,175,408 B2 * | 2/2007 | Watanabe et al. | ............. | 425/169 |
| 2001/0035431 A1 | 11/2001 | Runft | | |

FOREIGN PATENT DOCUMENTS

| | | |
|---|---|---|
| DE | 34 41 856 A1 | 10/1985 |
| DE | 195 04 019 A1 | 8/1995 |
| DE | 100 01 068 C1 | 5/2001 |
| EP | 0 837 313 A1 | 4/1998 |
| WO | WO 9825823 A1 * | 6/1998 |

* cited by examiner

*Primary Examiner* — Gregory Huson
*Assistant Examiner* — Jason Niesz

(57) ABSTRACT

A powder dispensing device is disclosed for dispensing powder into hard gelatin capsules or the like. The powder dispensing device comprises at least one plunger for compacting the powder to a powder compact and/or at least one transfer plunger which transfers the previously produced powder compact into a capsule part ready to be filled. The device includes a sensing apparatus including fiber-optical cables and a lens for introducing and receiving radiation passed through the powder or the powder compact. The sensing apparatus is connected to either the compacting plunger or the transfer plunger, or both.

20 Claims, 2 Drawing Sheets

SENSING APPARATUS

CROSS-REFERENCE TO RELATED APPLICATION

This application is a 35 USC 371 application of PCT/EP 2006/064575 filed on Jul. 24, 2006.

BACKGROUND OF THE INVENTION

1. Field of the Invention

The invention relates to a sensing apparatus, in particular in dispensing powder into hard gelatin capsules or the like.

2. Description of the Prior Art

From German Patent DE 100 01 068 C1, a dispensing device is known, which includes an incrementally rotated dispensing disk in the base of which boards are embodied which cooperate with stuffing dies that are movable up and down. The stuffing dies are disposed on a common stuffing die holder, and as they dip into the bores they press the powder into powder metal compacts. To detect spring breakage and to be able to draw a conclusion about the mass of the compacts, means are provided that detect the spring travel of the expulsion die at the immediately preceding stuffing die. In one exemplary embodiment, the stuffing dies directly preceding the expulsion dies are each provided with a travel pickup—such as a strain gauge or an inductive sensor. Thus both spring breakage and incorrect dosages can be detected.

SUMMARY OF THE INVENTION

The sensing apparatus of the invention has the advantage over the prior art that a qualitative conclusion is possible about such product parameters as the proportion of an active ingredient, quantitative quantity of an active ingredient, or product quantity. Thus product analysis of the compacts is made possible in a simple way; until now, this was done outside the apparatus by means of an analysis device.

DESCRIPTION OF THE PREFERRED EMBODIMENTS

Figure 1:
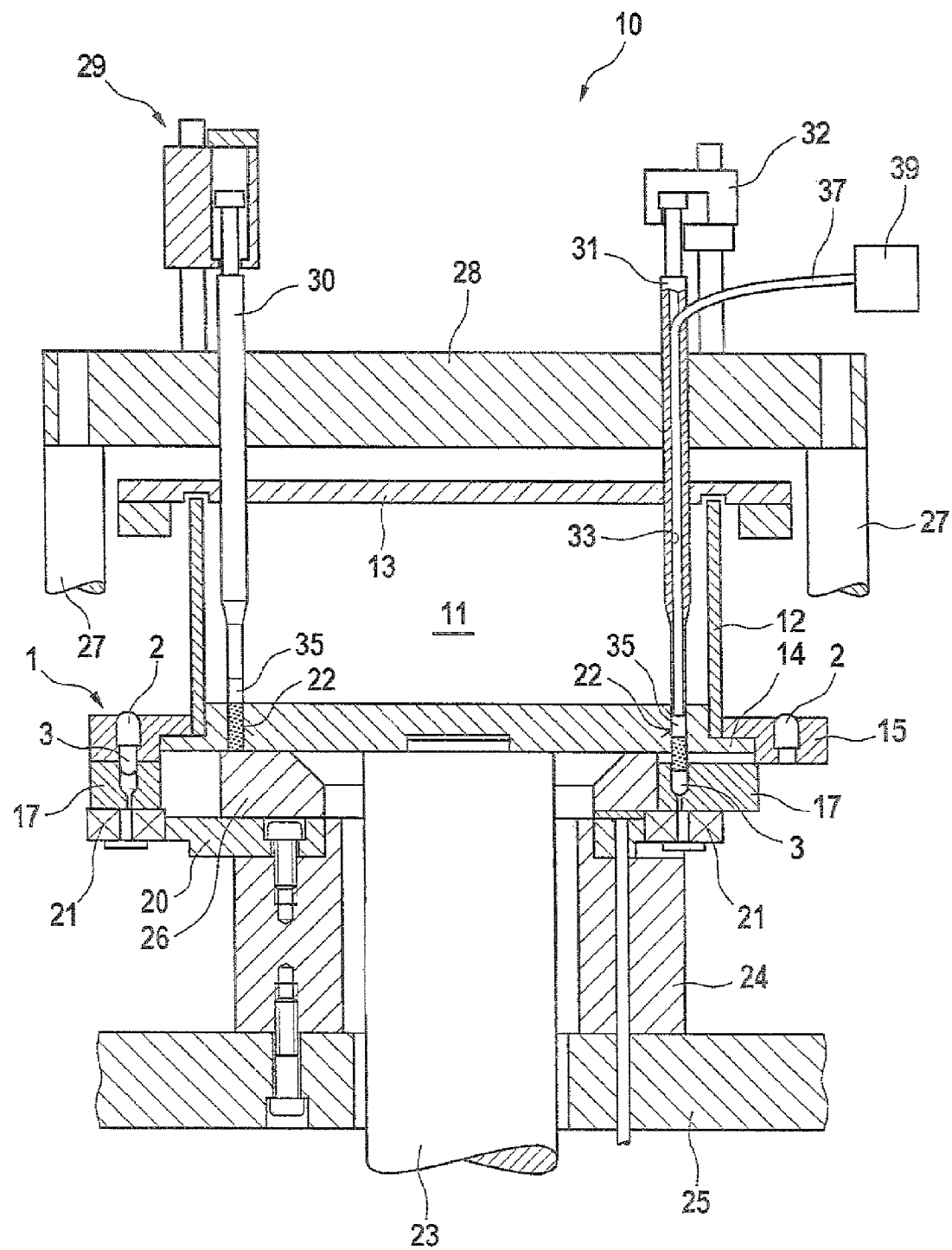
FIG. 1 shows a longitudinal section through a powder dispensing apparatus having sensing apparatus according to the invention.

The powder dispensing device 10 shown in FIG. 1 for dosing and dispensing powder into hard gelatine capsules 1 or the like has a product container 11. The product container 1 is formed by a jacket 12, a cap 13, and a dispensing disk 14. At the level of the dispensing disk 14, the product container 11 is surrounded by a ring 15, which serves to receive upper parts 2 of capsules. Below the ring 15 segments 17 are provided which are correspondingly embodied to receive lower parts 3 of capsules. The segments 17 are each supported pivotably about a bolt, not shown, that is secured in the ring 15, and upon circulating through a fixed curve 20, via a curve roller 21, are moved inward, that is, below bores 22 in the dispensing disk 14, or outward, that is, beyond the circumference of the ring 15, depending on requirements. The dispensing disk 14 is secured to a shaft 23 that is coupled to the drive of the device 10 and that rotates the dispensing disk 14 in increments of one angular amount each.

For fastening the curve 20, a second ring 24 is provided, which in turn is fastened to the tabletop 25 of the device 10. Between the curve 20 and the dispensing disk 14, an intermediate ring 26 is provided, which can be pressed by adjusting means, not shown, against the underside of the dispensing disk 14. This intermediate ring 26 serves to seal off the bores 22 in the dispensing disk 14 in the region where the powder is dispensed.

As FIG. 1 also shows, above the product container 11 is a holder 28, which is movable up and down by means of columns 27 and in each case executes a defined stroke. Along an arc of the holder 28, a plurality of stuffing die holders 29, for instance three stuffing die holders 29, are disposed at equal angular spacings, and in each of them five stuffing dies 30 are guided that penetrate the cap 13 of the product container 11 in corresponding bores. Expulsion dies or transfer dies 31 are also located on the holder 28 and are connected, in a height-adjustable manner, to a mount 32 disposed on the holder 28. The transfer dies 31 are surrounded inside the product container 11 by a powder-repellent body 33. A sensor 35 is disposed in the tip of the transfer die 31, for detecting such product parameters as the active ingredient proportion, quantitative active ingredient quantity, or product quantity. The sensor 35 is preferably embodied optically (infrared). A fiber-optical line 37 is disposed in a recess in the transfer die 31, so as to deliver the optical signal of the sensor 35 to a signal evaluator 39.

The device 10 described above functions as follows: For forming the compacts in the bores 22 from the powder located in the product container 11, the dispensing disk 14 is rotated clockwise in increments, in each case beneath the stuffing dies 30 of one stuffing die holder 29. Next, the stuffing dies 30, upon a downward motion of the holder 28, penetrate the bores 22 of the dispensing disk 14, and the powder located in the bore 22 is compacted. During the compacting or pressing of the powder, the intermediate ring 26 forms a counterpart bearing for the stuffing dies 30 or powder. Next, the stuffing dies 30 are moved back out of the bores 22 of the dispensing disk 14 by means of the holder 28, whereupon the dispensing disk 14 is rotated into the vicinity of the next stuffing die holder 29. After the final pressing operation, the thus-formed compacts reach the vicinity of the transfer dies 31, where they are inserted into the lower capsule parts 3 furnished by means of the segments 17. Next, the lower capsule parts 3 are rejoined to the upper capsule parts 2.

Figure 2:
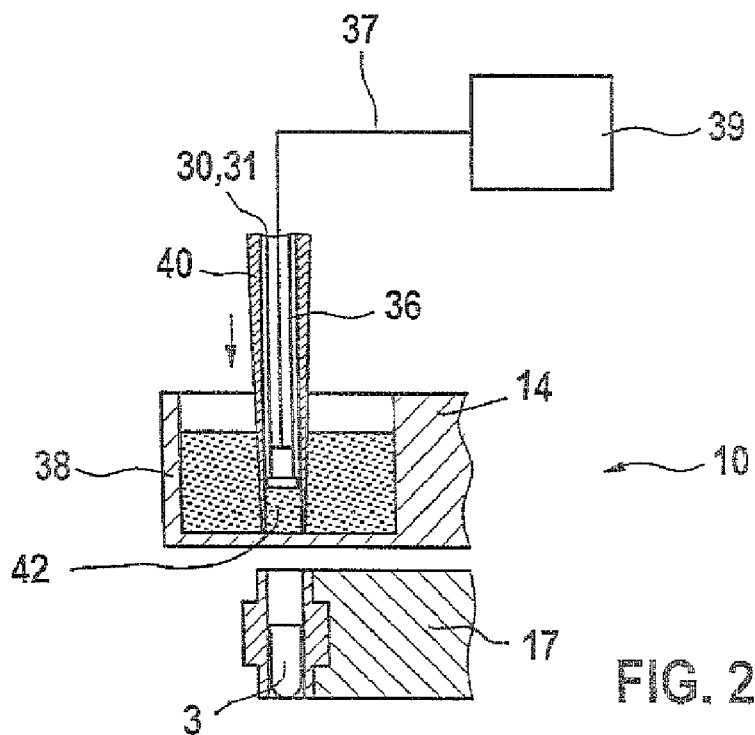
FIG. 2 shows a simplified view of the powder dispensing device with the sensing apparatus according to the invention.

In FIG. 2, a powder dispensing device based on the tubule principle, with a sensor array, is shown as an example. The stuffing die 30, comprising a cylinder 40 (or tubule) and a piston 36, is lowered into a rotary container 38 as far as the level of the product, this level being set (manually or by means of an actuator), via the segment containers. Next, the cylinder 40 is lowered into the product layer, while the piston 36 maintains its own position and forms the dosage chamber 42, set simultaneously beforehand to all dosages. The thus-set dispenser is lowered to the bottom of the rotary container 38, until the dosage chamber 42 is full. If necessary for the product in question, the desired compacting can now be done via the setting of the special cam (manually or by means of an actuator). The sensing can then preferably be done for further evaluation and determination of the product parameters of interest. After that, the piston 36 moves upward and is raised somewhat from the blank or compact. Next, the dispenser is raised above the rotary container 38 again and is oriented vertically with the lower capsule parts in the bushes. Next, the piston is lowered, and the product is introduced into the lower capsule part 3. This is followed by a new dispensing cycle.

Figure 3:
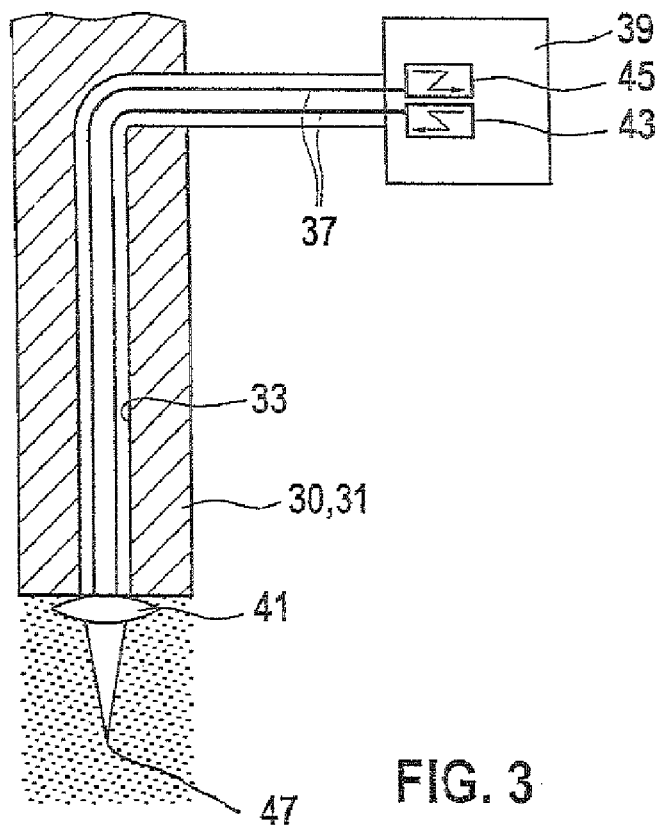
FIG. 3 shows a more-precise schematic illustration of the components of the sensing apparatus.

FIG. 3 in a more precise view now shows the basic construction of the sensing apparatus in section. In the stuffing die 30 or transfer die 31, the powder repellant body 33 is preferably a cylindrical recess provided in the middle thereof which extends in the direction of the axis of the die 30, 31 and ends in an opening in the tip of the die 30, 31. Two fiber-optical cables 37 are disposed in the recess. One fiber-optical cable 37 is connected to an optical transmitter 43; the other fiber-optical cable 37 is connected to an optical receiver 45. The optical transmitter 43 and optical receiver 45 are integrated in a signal detector 39, which is preferably equipped with triggering electronics and a triggering unit. The signal detector 39 is preferably located at a point remote from the dies 30, 31. The fiber-optical cables 37 conduct optical radiation into the product and receive the radiation, reflected by the product, via a lens 41. The lens 41 is preferably disposed in or at the opening in the die 30, 31.

As the lens 41, a convex lens is preferably employed. This produces a focal point 47 that is located inside the compact but not on its surface. As a result, dirt on the lens 41 does not in principle impair the quality of signal detection. The signal detector 39 initiates a measurement operation when the die 30, 31 reaches a defined position within a processing step. The optical transmitter 43 is then triggered in such a way that for a defined length of time, it outputs optical radiation to one of the glass fibers 37. This radiation, via the fiber-optical cables 37 and the lens 41, penetrates the product, such as the powder metal compact. The product reflects a portion of the introduced radiation. Via the lens 41 and the second fiber-optical cables 37, the reflected radiation reaches the optical receiver 45, which converts the optical signals into electrical signals. The signal detector 39 now assesses the signals received, as a function of the signals transmitted. Known methods of spectral analysis are employed, in which the wave spectra of the radiation received are evaluated. Qualitative conclusions about such product parameters as the active ingredient proportion, quantitative active ingredient quantity, or product quantity are thus made possible. Preferably, radiation in the infrared range is emitted.

Instead of carrying signals in and out by means of fiber-optical cables 37, transmitters 43 and receivers 45 could already be disposed in the die 30, 31, and the signals could be exchanged with the signal processor 39 in some other way, for instance electrically or in wireless fashion.

The foregoing relates to the preferred exemplary embodiments of the invention, it being understood that other variants and embodiments thereof are possible within the spirit and scope of the invention, the latter being defined by the appended claims.

The invention claimed is:

1. A powder dispensing device with a sensing apparatus, for dispensing powder into powder receiving containers, comprising:
   at least one compacting die for compacting the powder into a powder compact and/or at least one transfer die that transfers a previously formed powder compact into a prepared container part; and
   a sensing means within said at least one compacting die and/or said at least one transfer die for introducing and receiving radiation conducted through the powder or through the powder compact, the sensing apparatus connected to the compacting die or to the transfer die.

2. The device according to claim 1, further comprising at least one recess provided in the transfer die and/or the compacting die, wherein the sensing means for introducing and receiving radiation are disposed within the at least one recess.

3. The device according to claim 1, wherein the sensing means for introducing and receiving the radiation comprises a lens.

4. The device according to claim 2, wherein the sensing means for introducing and receiving the radiation comprises a lens.

5. The device according to claim 1, wherein the means for introducing and receiving the radiation comprises at least one fiber-optical cable.

6. The device according to claim 2, wherein the means for introducing and receiving the radiation comprises at least one fiber-optical cable.

7. The device according to claim 3, wherein the means for introducing and receiving the radiation comprises at least one fiber-optical cable.

8. The device according to claim 4, wherein the means for introducing and receiving the radiation comprises at least one fiber-optical cable.

9. The device according to claim 1, further comprising an optical transmitter and receiver both connected to the sensing means for introducing and receiving radiation.

10. The device according to claim 2, further comprising an optical transmitter and receiver both connected to the sensing means for introducing and receiving radiation.

11. The device according to claim 3, further comprising an optical transmitter and receiver both connected to the sensing means for introducing and receiving radiation.

12. The device according to claim 4, further comprising an optical transmitter and receiver both connected to the sensing means for introducing and receiving radiation.

13. The device according to claim 5, further comprising an optical transmitter and receiver both connected to the sensing means for introducing and receiving radiation.

14. The device according to claim 1, wherein a process of measuring received radiation is performed during or immediately after compacting the powder.

15. The device according to claim 1, further comprising a signal processor connected to the sensing means, the signal processor ascertaining a quantity of powder, a quantity of an active ingredient, and/or a proportion of an active ingredient in the powder or the powder compact, as a function of radiation received from the sensing means.

16. The device according to claim 2, further comprising a signal processor connected to the sensing means, the signal processor ascertaining a quantity of powder, a quantity of an active ingredient, and/or a proportion of an active ingredient in the powder or the powder compact, as a function of radiation received from the sensing means.

17. The device according to claim 3, further comprising a signal processor connected to the sensing means, the signal processor ascertaining a quantity of powder, a quantity of an active ingredient, and/or a proportion of an active ingredient in the powder or the powder compact, as a function of radiation received from the sensing means.

18. The device according to claim 4, further comprising a signal processor connected to the sensing means, the signal processor ascertaining a quantity of powder, a quantity of an active ingredient, and/or a proportion of an active ingredient in the powder or the powder compact, as a function of radiation received from the sensing means.

19. The device according to claim 15, wherein the signal processor as a function of the radiation received from the sensing means, ascertains the quantity of powder, the quantity of an active ingredient, and/or the proportion of active ingredient in the powder or the powder compact by spectral analysis.

20. The device according to claim 3, wherein the lens is embodied as a convex lens.

* * * * *